United States Patent [19]
Hasegawa et al.

[11] Patent Number: 6,072,083
[45] Date of Patent: Jun. 6, 2000

[54] METHOD FOR PURIFYING BRANCHED CHAIN AMINO ACIDS

[75] Inventors: Kazuhiro Hasegawa; Yutaka Okamoto; Toru Nakamura; Tetsuya Kaneko; Chiaki Sano; Kinzo Iitani, all of Kawasaki, Japan

[73] Assignee: Ajinomoto Co., Inc., Tokyo, Japan

[21] Appl. No.: 09/030,955

[22] Filed: Feb. 26, 1998

[30] Foreign Application Priority Data

Feb. 26, 1997 [JP] Japan .................................. 9-041980

[51] Int. Cl.⁷ .................................................. C09C 227/00
[52] U.S. Cl. .................................................. 562/554
[58] Field of Search .......................................... 562/554

[56] References Cited

FOREIGN PATENT DOCUMENTS 2178879  12/1996  Canada .
52-3016  1/1977  Japan .

*Primary Examiner*—Gary Geist
*Assistant Examiner*—Taylor V Oh
*Attorney, Agent, or Firm*—Oblon, Spivak, McClelland, Maier & Neustadt, P.C.

[57] ABSTRACT

A method for purifying an amino acid selected from the group consisting of valine, leucine and isoleucine easily in high yield and with high purity using an inexpensive precipitant, comprising allowing p-ethylbenzenesulfonic acid or its water-soluble salt to act on an aqueous solution containing an amino acid to form crystals of the amino acid p-ethylbenzenesulfonate and then separating and decomposing the crystals to purify and obtain the amino acid. The p-ethylbenzenesulfonic acid may be used as the free acid, an alkali metal salt and an ammonium salt.

6 Claims, 4 Drawing Sheets

METHOD FOR PURIFYING BRANCHED CHAIN AMINO ACIDS

FIELD OF THE INVENTION

The present invention relates to novel valine ethylbenzenesulfonate salt crystals suitable for purification of valine, to a method for purifying valine by use of the salt, to novel leucine ethylbenzenesulfonate salt crystals suitable for purification of leucine, and a method for purifying leucine by use of the salt, and to novel isoleucine ethylbenzenesulfonate salt crystals suitable for purification of isoleucine and a method for purifying isoleucine by use of the salt.

BACKGROUND OF THE INVENTION

Valine is useful as a starting material for pharmaceutical amino acid preparations, as a synthetic intermediate for various pharmaceutical preparations and as an intermediate for chemicals such as agricultural chemicals.

Leucine is useful as a starting material for pharmaceutical amino acid preparations, nutrients, and as a synthetic intermediate for various pharmaceutical preparations.

Isoleucine is useful as a starting material for pharmaceutical amino acid preparations, nutrients, and as a synthetic intermediate for various pharmaceutical preparations.

In general, valine, leucine and isoleucine are generically called branched chain amino acids.

Valine is produced by hydrolyzing proteins such as soybean protein or by a method of culturing a microorganism having the ability to produce valine. The conventional methods of isolating and purifying valine from aqueous, valine-containing solutions such as protein hydrolysates, fermentation broth etc. obtained in these methods include:

(1) a method of removing neutral amino acids other than valine by repeatedly re-crystallizing the neutral amino acid fraction collected by separating and removing from acidic and basic amino acids by treatment with ion exchange resins (Biochem. J., 48, 313 (1951)); and (2) a method of adding hydrochloric acid to an aqueous solution containing valine and then repeatedly forming and precipitating crystals of valine hydrochloride (Japanese Patent Application Laid-Open Publication No. 16450/81). However, there are the problems that the former method is very cumbersome in operation and difficult to separate valine from leucine and isoleucine, while the latter results in lower yield because of the high solubility of crystals of valine hydrochloride in water.

Other valine purification methods include precipitating an adduct (slightly soluble salt) selectively with valine. For example, tetrachloro-orthophthalic acid, sulfoisophthalic acid, flavian (phonetic) acid amenol "flavianic acid" (Japanese Patent Publication No. 25059/67), or p-isopropylbenzenesulfonic acid (Japanese Patent Application Laid-Open Publication No. 333,312/96), is allowed to form an adduct with valine in order to purify valine. However, there are the problems that the precipitants used for valine: tetrafluorophthalate, sulfoisophthalate, and flavianate, are expensive and hard to obtain industrially, and the solubility of the resulting adduct is so high that recovery of valine in high yield is difficult so these methods of isolating valine from the adduct are cumbersome. On the other hand, p-isopropylbenzenesulfonic acid is very effective as a precipitant for valine, but there are the problems that p-isopropylbenzenesulfonic acid itself is not capable of decomposition with active sludge, so disposal of its waste fluid is difficult. Because of its hard formation of a sparingly soluble salt with isoleucine, it cannot be applied to other branched chain amino acids and so its use is limited.

Leucine is produced by a method of hydrolyzing proteins such as soybean protein or by a method of culturing a microorganism having the ability to produce leucine. The conventional methods of isolating and purifying leucine from aqueous, leucine-containing solutions such as protein hydrolysates, fermentation broth obtained in these methods include:

(1) a method of removing neutral amino acids other than leucine by repeatedly re-crystallizing the neutral amino acid fraction collected by separating and removing acidic and basic amino acids by treatment with ion exchange resins (Biochem. J., 48, 313 (1951)); and (2) a method of adding hydrochloric acid to an aqueous solution containing leucine and then repeatedly forming and precipitating crystals of leucine hydrochloride (Experimental Chemistry Lecture, Vol. 23, Biochemistry I, 75, compiled by the Chemical Society of Japan and published by Maruzen (1957)). However, there are the problems that the former is very cumbersome in operation and it is difficult to separate leucine from valine and isoleucine, while the latter results in lower yield because of the high solubility of crystals of leucine hydrochloride in water.

Other leucine purification methods include precipitating an adduct (slightly soluble salt) selectively with leucine. For instance, naphthalene β-sulfonic acid, 2-bromotoluene-5-sulfonic acid (Experimental Chemistry Lecture, Vol. 23, Biochemistry I, 75, compiled by the Chemical Society ol Japan and published by Maruzen (1957)), 1,2-dimethylbenzene-4-sulfonic acid (Japanese Patent Application Laid-Open Publication No. 11373/65), benzenesulfonic acid (Japanese Patent Application Laid-Open Publication No. 149,222/76), or p-toluenesulfonic acid (Japanese Patent Application Laid-Open Publication No. 3016/77), is allowed to form art adduct with leucine in order to purify leucine. However, there are the problems that the precipitants used for leucine naphthalene P-sulfonate and 2-bromotoluene-5-sulfonate are expensive and hard to obtain industrially, and the solubility of the resulting adduct is so high that recovery of leucine in high yield is difficult, and the method of isolating leucine from the adduct is cumbersome. On the other hand, 1,2-dimethylbenzene-4-sulfonic acid, benzene sulfonic acid and p-toluenesulfonic acid are very effective as precipitants for leucine, but 1,2-dimethylbene-4-sulfonic acid hardly forms a slightly soluble salt with valine and isoleucine; benzene sulfonic acid hardly forms a slightly soluble salt with isoleucine; and p-toluenesulfonic acid hardly forms a sparingly soluble salt with valine, so their limited use is disadvantageous.

Isoleucine is produced by a method of hydrolyzing proteins, such as soybean protein or by a method of culturing a microorganism having the ability to produce isoleucine. The conventional methods of isolating and purifying isoleucine from aqueous, isoleucine-containing solutions such as protein hydrolysates and fermentation broth obtained in these methods include:

(1) a method of removing neutral amino acids other than isoleucine by repeatedly re-crystallizing the neutral amino acid fraction collected by separating and removing acidic and basic amino acids by treatment with ion exchange resins (Biochem. J., 48, 313 (1951)); and (2) a method of adding hydrochloric acid to an aqueous solution containing isoleucine and then repeatedly forming and precipitating crystals of isoleucine hydrochloride (J. Biologc. Chem., 118, 78 (1973)). However, there are the problems that the former method is very cumbersome in operation and difficult to separate isoleucine from valine and leucine, while the latter method results in lower yield because of the high solubility of crystals of isoleucine hydrochloride in water.

Other isoleucine purification methods include precipitating an adduct (sparingly soluble salt) selectively with isoleucine. For instance, 4-nitro-4'-methyldiphenylamine-2-sulfonic acid (J. Biologc. Chem., 143, 121 (1942)), 2-naphthol-6-sulfonic acid (Japanese Patent Application Laid-Open Publication No. 13515/73), or 1,5-napthalenedisulfonic acid (Japanese Patent Application Laid-Open Publication No. 109,953/79), is allowed to form an adduct in order to purify isoleucine. However, there are the problems that the precipitants are expensive and hard to obtain industrially, the method of isolating isoleucine from the adducts is cumbersome, difficult formation of salts with amino acids other than isoleucine makes their usage limited, and the toxicity of the precipitants themselves is high.

SUMMARY OF THE INVENTION

An object of the present invention is to provide a method for purifying valine, leucine and isoleucine easily in high yield and with high purity using an inexpensive precipitant. Another object is to provide a precipitant that is applicable to any of valine, leucine and isoleucine, which due to their similar chemical properties are hard to separate and purify from each other, the precipitant being capable of assimilation with active sludge and being used readily in industry.

DESCRIPTION OF THE PREFERRED EMBODIMENTS

Figure 1:
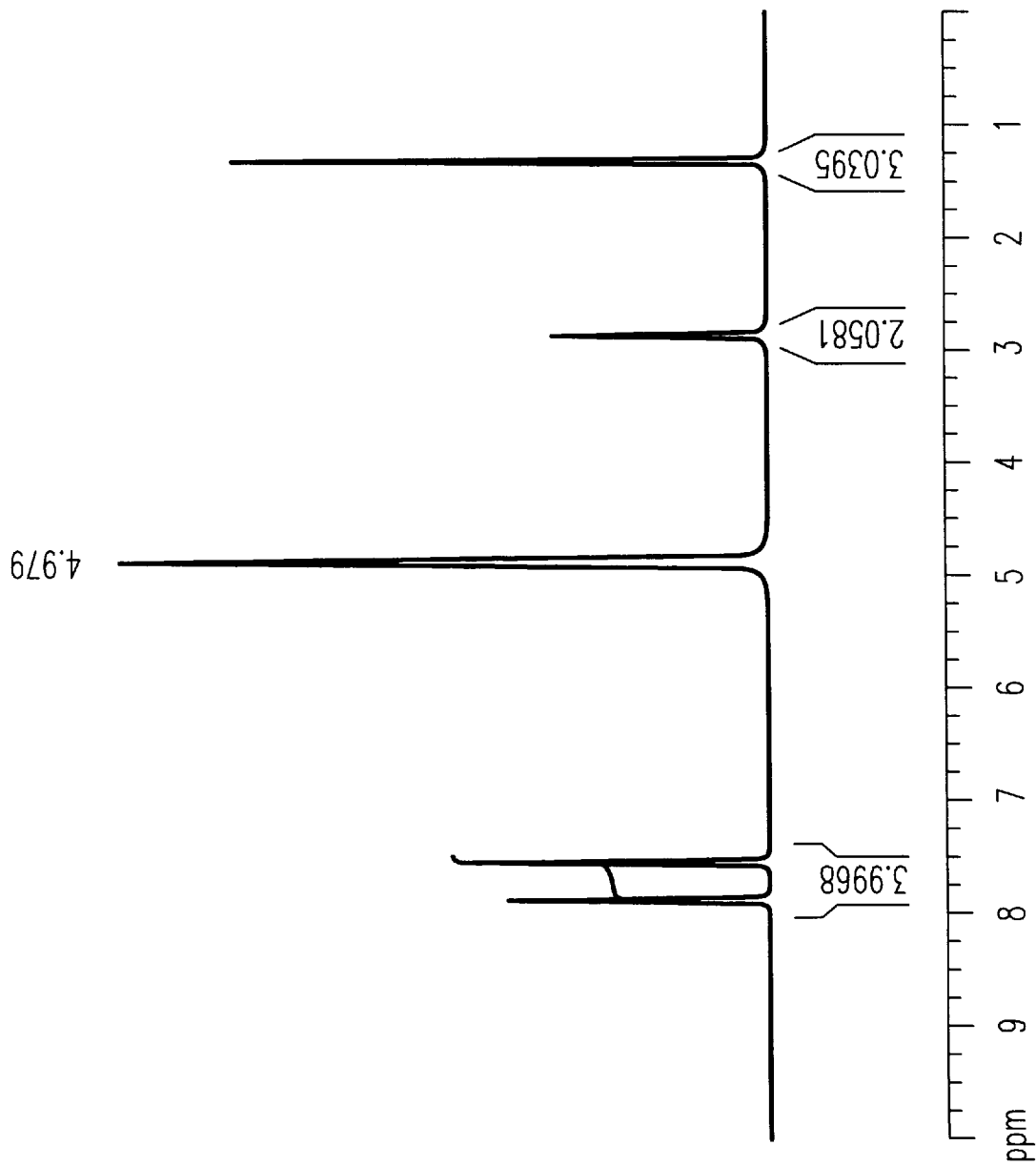
FIG. 1 is a $^1$H-NMR spectrum ($D_2O$) of sodium p-ethylbenzene sulfonate obtained in Reference Example 1.

The present inventors have fi)und that salt crystals of amino acid/p-ethylbenzene sulfonate are selectively precipitated by adding p-ethylbenzenesulfonic acid to an aqueous solution containing an amino acid selected from the group consisting of valine, leucine, and isoleucine, then reacting and cooling them.

The present invention comprises:

(1) Novel valine p-ethylbenzenesulfonate salt crystals comprising 1 mole of valine and 1 mole of p-ethylbenzene sulfonic acid, and (2) A method for purifying valine, which comprises adding p-ethylbenzenesulfonic acid or its water-soluble salt to an aqueous solution containing valine to form and precipitate salt crystals of valine p-ethylbenzenesulfonate and then separating and decomposing the salt crystals to obtain valine.

(3) Novel leucine p-ethylbenzenesulfonate crystals comprising 1 mole of leucine and 1 mole of p-ethylbenzene sulfonic acid, and (4) A method for purifying leucine, which comprises adding p-ethylbenzenesulfonic acid or its water-soluble salt to an aqueous solution containing leucine to form and precipitate crystals of leucine p-ethylbenzenesulfonate and then separating and decomposing said salt to obtain leucine.

(5) Novel isoleucine p-ethylbenzenesulfonate crystal comprising 1 mole of isoleucine and 1 mole of p-ethylbenzene sulfonic acid, and (6) A method for purifying isoleucine, which comprises adding p-ethylbenzenesulfonic acid or its water-soluble salt to an aqueous solution containing isoleucine to form arid precipitate salt crystals of isoleucine p-ethylbenzene sulfonate and then separating and decomposing said salt crystals to obtain isoleucine.

The valine, leucine or isoleucine to which the present method can be applied, may be the optically active isomers (L or D isomers), the racemate, or a mixture thereof. The aqueous solution containing valine, leucine or isoleucine includes a wide variety of aqueous solutions such as a mixture of amino acids obtained by separating and removing basic amino acids from a hydrolysate where proteins, such as soybean protein, have been hydrolyzed, a fermentation broth obtained by culturing a microorganism having the ability to produce and accumulate valine, leucine or isoleucine, or a liquid obtained by removing the microorganism from the fermentation liquid, or a liquid obtained by treating it with ion exchange resin or adsorption resin, or an aqueous solution of crude D,L-valine, D,L-leucine or D,L-isoleucine obtained e.g. via a hydantoin derivative by a chemical synthesis method.

p-Ethylbenzenesulfonic acid used in the present invention can be easily produced by placing ethylbenzene and 1.5 molar excess of concentrated sulfuric acid in a glass vessel and heating the mixture at 130° C. for 1 to 2 hours, so it can be obtained inexpensively in industry. p-Ethylbenzenesulfonic acid can be used as the free acid or in the form of its water-soluble salts, for example alkali metal salts such as sodium salt, potassium salt, etc., alkaline earth metal salts such as calcium salt, etc., or ammonium salts. The amount of p-ethylbenzene sulfonic acid or its water-soluble salt used is equimolar or more, preferably 1.0 to 1.1-fold molar excess relative to valine, leucine or isoleucine contained in the aqueous solution, and a particularly large excess is not required.

The desired compound, valine p-ethylbenzenesulfonate, can be easily formed and precipitated by adding p-ethylbenzenesulfonic acid or its water-soluble salt to an aqueous solution containing 60 g/L or more valine and adjusting it to about pH 1.5. The pH of the solution suitable for forming and precipitating the crystals of valine p-ethylbenzenesulfonate is in the range of 0.1 to 2.3, preferably 1.0 to 1.7. The acid used for pH adjustment is an inorganic acid such as hydrochloric acid, sulfuric acid. If necessary, seed crystals of valine p-ethylbenzenesulfonate. can be added to a mixture solution of valine and p-ethylbenzenesulfonic acid to efficiently precipitate crystals. If a dilute solution is used as the aqueous solution of valine, it may be concentrated to precipitate crystals of the salt. In this case, p-ethylbenzenesulfonic acid may be added in any stage before or after concentration. Although crystals of free valine are precipitated if the aqueous solution of valine is concentrated at neutrality, crystals of valine p-ethylbenzenesulfonate can be easily formed by adding a suitable amount of p-ethylbenzenesulfonic acid and adjusting it to about pH 1.5. Alternatively, a dilute solution of valine in the coexistence of a suitable amount of p-ethylbenzenesulfonic acid may be concentrated to precipitate crystals of valine p-ethylbenzenesulfonate after adjusting it to about pH 2.

To separate and obtain the precipitated crystals of valine p-ethylbenzenesulfonate, conventional methods for solid-liquid separation, for example, filtration and centrifugation may be used. Although the separated crystals are of high purity, they can further be purified by conventional purification methods such as rinsing and re-crystallizing.

The resulting valine p-ethylbenzenesulfonate crystal consisting of 1 mole of valine and 1 mole of p-ethylbenzene sulfonic acid is a novel substance with the following physical properties:
White plate crystal: soluble in water and ethanol.
Solubility in water: 14.5 wt % (pH 1.4, 5° C.)
Crystal structure: rhombic system
Crystal density: 1.31 g/cm$^3$
Elemental analysis: C, 51.6%; H, 6.9%; N, 4.5%; S, 10.5%. (calc.: C, 51.5% H, 6.9%; N, 4.6%; S, 10.6%)

To isolate free valine from the crystals of valine p-ethylbenzenesulfonate, the crystals are dissolved in a large amount of hot water, and then the solution may be contacted with weakly basic ion exchange resin (OH form), or an alkali such as sodium hydroxide may be added to the solution. If ion exchange resin is used, p-ethylbenzenesulfonic acid is adsorbed onto it to give free valine as an eluting solution. It is subjected to conventional methods e.g. crystallization by concentration to give valine crystals. The precipitant (p-ethylbenzenesulfonic acid) adsorbed onto the resin is eluted as alkali salt upon regeneration of the resin with an alkali solution such as sodium hydroxide solution.

In the method of adding an alkali, an alkali such as sodium hydroxide is added as itself or an aqueous solution of it to an aqueous suspension of crystals of valine p-ethylbenzenesulfonate, then the pH is adjusted in the range of about 5 to 8, preferably 6 to 7, whereby p-ethylbenzenesulfonic acid is dissolved in the solution as an alkali salt while free valine is precipitated, and the precipitated valine is separated from the solution.

The precipitant (p-ethylbenzenesulfonic acid) itself separated and recovered as the alkali salt can be used again as the precipitant in the next operation.

The desired compound, leucine p-ethylbenzenesulfonate, can be easily formed and precipitated by adding p-ethylbenzenesulfonic acid or its water-soluble salt to an aqueous solution containing 30 g/L or more leucine and adjusting it to about pH=1.5. The pH of the solution suitable forming and precipitating the crystals of leucine p-ethylbenzenesulfonate is in the range of 0.1 to 2.3, preferably 1.0 to 1.7. The acid used for pH adjustment is an inorganic acid such as hydrochloric acid and sulfuric acid. If necessary, seed crystals of leucine p-ethylbenzenesulfonate can be added to a mixture solution of p-ethylbenzenesulfonic acid to efficiently precipitate crystals. If a dilute solution is used as the aqueous solution of leucine, it may be concentrated to precipitate crystals of the salt. In this case, p-ethylbenzenesulfonic acid may be added at any stage before or after concentration. Although crystals of free leucine are precipitated if the aqueous solution of leucine is concentrated at neutrality, crystals of leucine p-ethylbenzenesulfonate can be easily formed by adding a suitable amount of p-ethylbenzenesulfonic acid and adjusting it to about pH=1.5. Alternatively, a dilute solution of leucine in the coexistence of a suitable amount of p-ethylbenzenesulfonic acid may be concentrated to precipitate crystals of leucine p-ethylbenzenesulfonate after adjusting it to about pH 2.

To separate and obtain the precipitated crystals of leucine p-ethylbenzenesulfonate, conventional methods for solid-liquid separation, for example, filtration and centrifugation may be used. Although the separated crystals are of high purity, they can be further purified by conventional purification methods such as rinsing and re-crystallizing.

The resulting leucine p-ethylbenzene sulfonate crystal consisting of 1 mole of leucine and 1 mole of p-ethylbenzene sulfonic acid is a novel substance with the following physical properties:
White plate crystal: soluble in water and ethanol.
Solubility in water: 7.1 wt % (pH 1.6, 5° C.)
Crystal structure: monoclinic system
Crystal density: 1.32 g/cm$^3$
Elemental analysis: C, 53.1%; H, 7.3%; N, 4.3%; S, 9.9%. (calc.: C, 53.0%; H, 7.3%; N, 4.4%; S, 10.1%)

To isolate free leucine from the crystals of leucine p-ethylbenzenesulfonate, the method of isolating free valine from crystals of valine p-ethylbenzenesulfonate as described above may be followed.

The precipitant (p-ethylbenzenesulfonic acid) itself separated and recovered as an alkali salt can be used again as the precipitant in the next operation.

The desired compound, isoleucine p-ethylbenzenesulfonate, can be easily formed and precipitated by adding p-ethylbenzene sulfonic acid or its water-soluble salt to an aqueous solution containing 50 g/L or more isoleucine and adjusting it to about pH 1.5. The pH of the solution suitable for forming and precipitating the crystals of isoleucine p-ethylbenzene sulfonate is in the range of 0.1 to 2.3, preferably 1.0 to 1.7. The acid used for pH adjustment is an inorganic acid such as hydrochloric acid and sulfuric acid. If necessary, seed crystals of isoleucine p-ethylbenzenesulfonate can be added to a mixture solution of isoleucine and p-ethylbenzenesulfonic acid to efficiently precipitate crystals. If a dilute solution is used as the aqueous solution of isoleucine, it may be concentrated to precipitate crystals of the salt. In this case, p-ethylbenzenesulfonic acid may be added in any stage before or after concentration. Although crystals of free isoleucine are precipitated if the aqueous solution of isoleucine is concentrated at neutrality, crystals of isoleucine p-ethylbenzenesulfonate can be easily formed by adding a suitable amount of p-ethylbenzenesulfonic acid and adjusting it to about pH 1.5. Alternatively, a dilute solution of isoleucine in the coexistence of a suitable amount of p-ethylbenzenesulfonic acid may be concentrated to precipitate crystals of isoleucine p-ethylbenzene sulfonate after adjusting it to about pH 2.

To separate and obtain the precipitated crystals of isoleucine p-ethylbenzene sulfonate, conventional methods for solid-liquid separation, for example, filtration and centrifugation may be used. Although the separated crystals are of high purity, they can be further purified by conventional purification methods, such as rinsing and re-crystallizing.

The resulting isoleucine p-ethylbenzenesulfonate crystal consisting of 1 mole of isoleucine and 1 mole of p-ethylbenzenesulfonic acid is a novel substance with the following physical properties:
White plate crystal: soluble in water and ethanol.
Solubility in water: 11.6 wt % (pH 1.5, 5° C.)
Crystal structure: monoclinic system
Crystal density: 1.27 g/cm$^3$
Elemental analysis: C, 53.1%; H, 7.3%; N, 4.3%; S, 9.8%. (calc.: C, 53.0%; H, 7.3%; N, 4.4%; S, 10.1%)

To isolate free isoleucine from the crystals of isoleucine p-ethylbenzenesulfonate, the method of isolating free valine from crystals of valine p-ethylbenzenesulfonate as described above may be followed.

The precipitant (p-ethylbenzenesulfonic acid) itself separated and recovered as an alkali salt can be used again as the precipitant in the next operation.

EXAMPLES

Hereinafter, the present invention is described in more detail by reference to examples. The quantification of leucine, isoleucine, valine and other amino acids was carried out with a Hitachi L-8500 type amino acid analyzer.

Reference Example 1 (Production and Assimilability of p-Ethylbenzenesulfonic Acid)

33 ml (0.6 mol) of conc. sulfuric acid was added to 62 ml (0.5 mol) of ethylbenzene, and the mixture was stirred for 1.5 hours under heating at 120 to 130° C. Layer separation will occur if unreacted ethylbenzene still remains, so the reaction was terminated when no layer separation was confirmed, and a solution containing p-ethylbenzenesulfonic acid as the major component was thus obtained. This solution was poured into 150 ml water and neutralized partially with sodium hydrogen carbonate, and the sodium chloride was added to precipitate crystals of sodium p-ethylbenzene sulfonate. The resulting crystals were separated by filtration and dried in vacuo. This sodium p-ethylbenzenesulfonate is easily soluble in water and sparingly soluble in ethanol. A $^1$H-NMR spectrum of the resulting crystals is shown in FIG. 1.

With respect to the ability of p-ethylbenzenesulfonic acid to be assimilated by active sludge, it has been confirmed that about 80% of 100 mg/L p-ethylbenzenesulfonic acid is assimilated for 2 weeks at pH 7.0 at a temperature of 25° C. ("Yukagaku" (Oil Chemistry), 28(5), 354 (1979)).

Example 1

Figure 2:
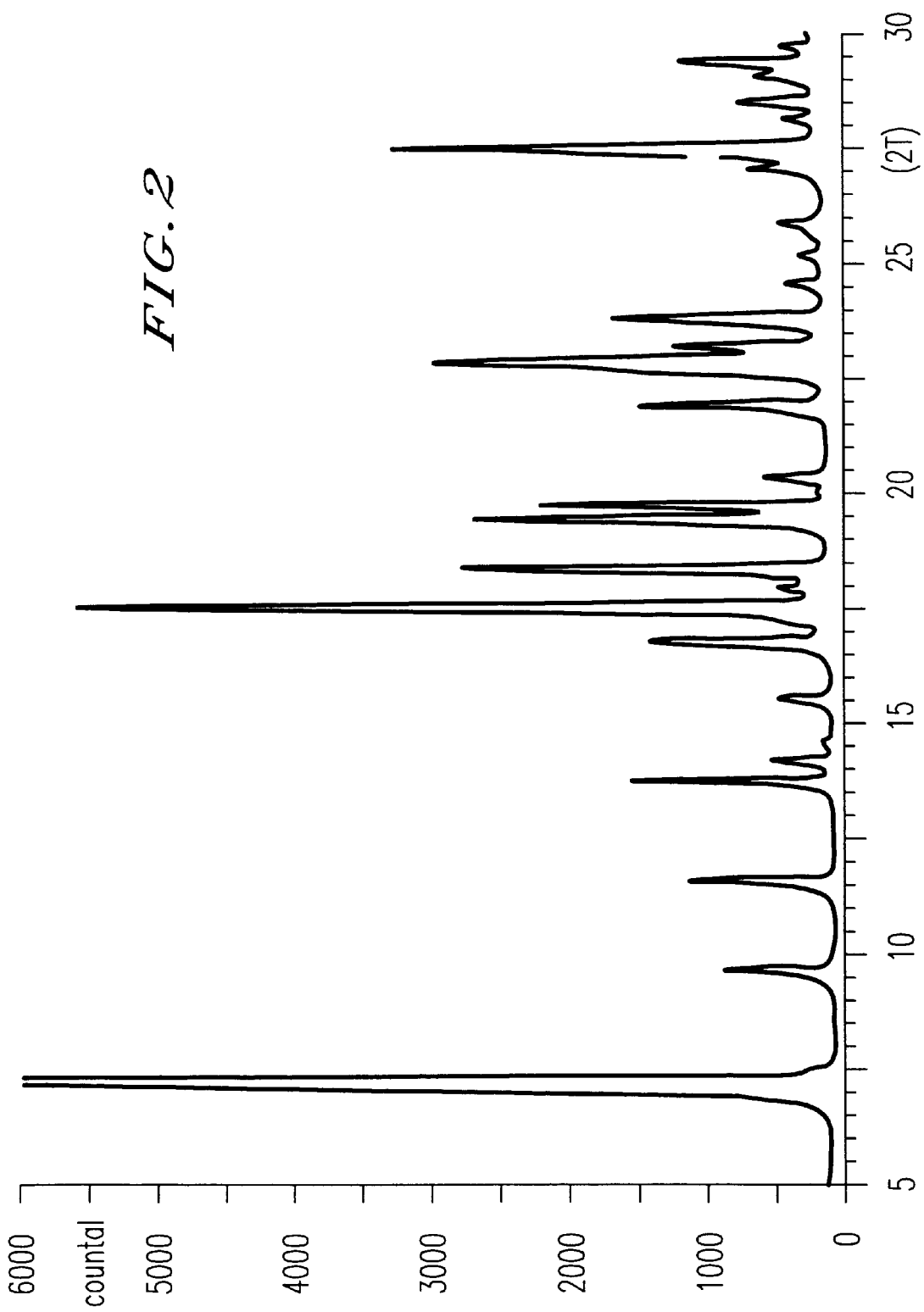
FIG. 2 is an X-ray diffraction pattern of the crystal powder of L-valine p-ethylbenzene sulfonate obtained in Example 1.

400 ml water was added to 100 g of L-valine and 159 g of p-ethylbenzenesulfonic acid, and the temperature of the solution was made 40° C. to dissolve the solid. Then, the solution was cooled it 5° C. to precipitate L-valine p-ethylbenzenesulfonate crystals, and the precipitated crystals were separated by filtration and then dried in vacuo. The resulting L-valine p-ethylbenzenesulfonate was fine white crystal in the rhombic system with 1.31 g/cm$^3$ crystal density. An X-ray diffraction pattern of the crystal powder is shown in FIG. 2. The X-ray diffraction was determined using Cu—Kα ray as a radiation source. The result of elemental analysis was C, 51.6%; H, 7.0%; N, 4.5%; S, 10.5%.

Comparative Example 1

400 ml water was added to 100 g of L-valine and 147 g of p-toluenesulfonic acid, and the temperature of the solution was made 40° C. to dissolve the solid. Then, the solution was cooled at 5° C., but no crystal was obtained.

Example 2

35 g of L-valine and 3.5 g each of L-leucine and L-isoleucine were dispersed in 125 ml water, and 55.6 g of p-ethylbenzenesulfonic acid (equimolar to valine) was added thereto, dissolved by heating, and adjusted to pH 1.1. Then, the solution was cooled to precipitate L-valine p-ethylbenzenesulfonate crystals. The precipitated crystals were recovered by centrifugation, then dissolved in a large amount of hot water, and passed through weakly basic ion exchange resin (OH form) to remove the p-ethylbenzenesulfonic acid. The eluate was crystallized by concentration to give 21 g of free L-valine crystals. Analysis of the mother liquor indicated that the ratio of precipitation of valine was 63%, the purity of free L-valine was 92%, and the content of the other amino acids was 8% or less, and 76% of the impurities before crystallization were removed.

Example 3

35 g of L-valine and 1.1 g each of L-leucine and L-isoleucine were dispersed in 100 ml water, and 55.6 g of p-ethylbenzenesulfonic acid (equimolar to valine) was added thereto, dissolved by heating, and adjusted to pH 1.1. Then, the solution was cooled to precipitate L-valine p-ethylbenzenesulfonate crystals. The precipitated crystals were recovered by centrifugation, then dissolved in a large amount of hot water, and passed through weakly basic ion exchange resin (OH form) to remove the p-ethylbenzenesulfonic acid. The eluate was crystallized by concentration to give 27 g of free L-valine crystals. Analysis of the mother liquor indicated that the ratio of precipitation of valine was 80%, the purity of free L-valine was 97%, and the content of the other amino acids was 3% or less, and 67% of the impurities before crystallization were removed.

Example 4

10 g of D-valine and 0.3 g each of D-leucine and D-isoleucine were added to 30 ml water, and 15.8 g of p-ethylbenzenesulfonic acid (equimolar to valine) was added thereto, adjusted to pH 1.1, and dissolved by heating. Then, the solution was cooled to precipitate D-valine p-ethylbenzenesulfonate crystals. The precipitated crystals were recovered by centrifugation, then dissolved in a large amount of hot water, and passed through weakly basic ion exchange resin (OH form) to remove the p-ethylbenzenesulfonic acid. The eluate was crystallized by concentration to give 7.5 g of free D-valine crystals. Analysis of the mother liquor indicated that the ratio of precipitation of valine was 80%, the purity of free D-valine was 97%, and the content of the other amino acids was 3% or less, and 67% of the impurities before crystallization were removed.

Example 5

Figure 3:
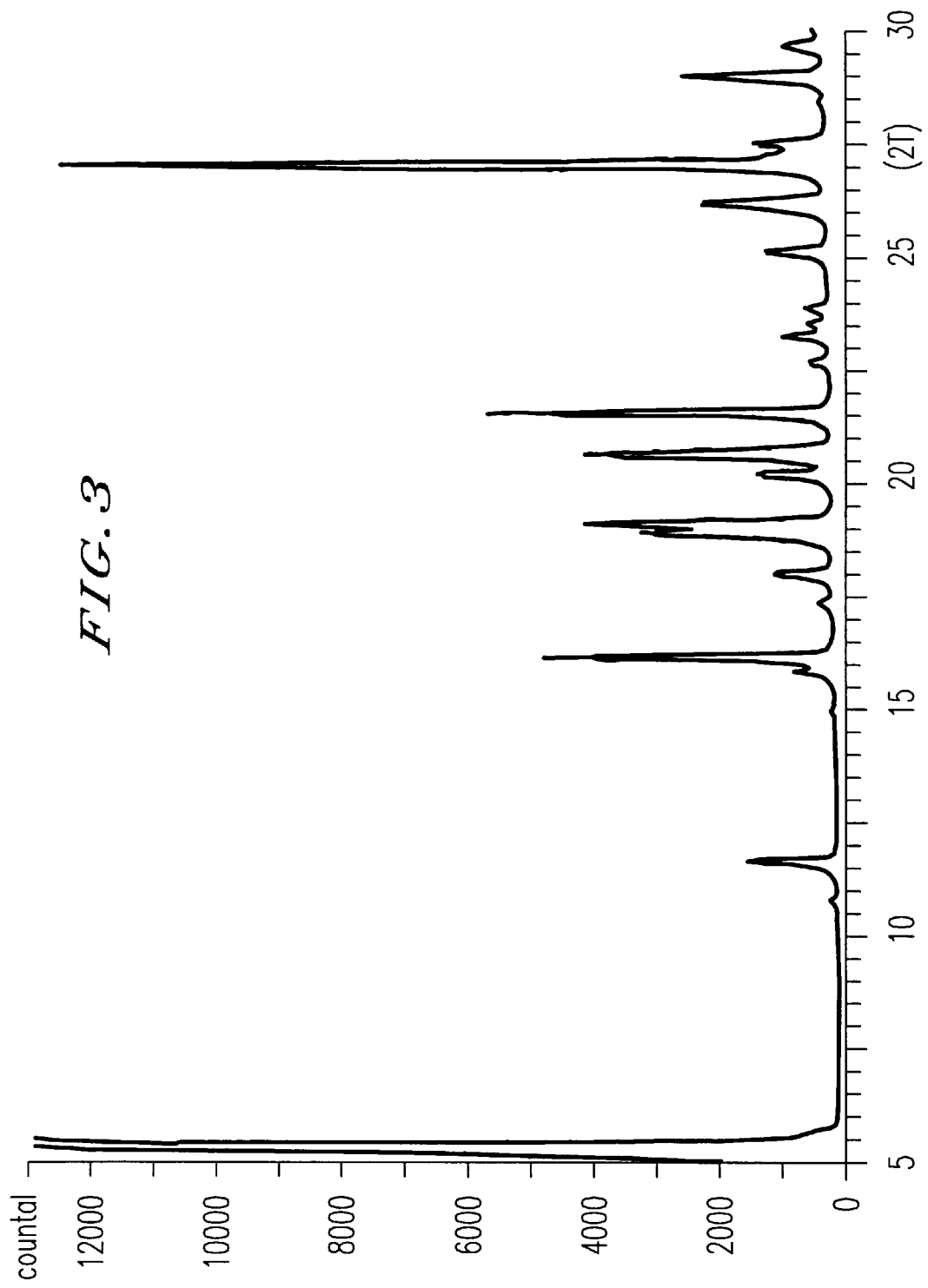
FIG. 3 is an X-ray diffraction pattern of the crystal powder of L-leucine p-ethylbenzene sulfonate obtained in Example 5.

400 ml water was added to 100 g of L-leucine and 142 g of p-ethylbenzenesulfonic acid, and the temperature of the solution was made 40° C. to dissolve the solid. Then, the solution was cooled at 5° C. to precipitate L-leucine p-ethylbenzenesulfonate crystals, and the precipitated crystals were separated by filtration and then dried in vacuo. The resulting L-leucine p-ethylbenzenesulfonate was fine white crystal in the monoclinic system with 1.32 g/cm$^3$ of a crystal density. An X-ray diffraction pattern of the crystal powder is shown in FIG. 3. The X-ray diffraction was determined using Cu—Kα ray as a radiation source. The result of elemental analysis was C, 53.0%; H, 7.4%; N, 4.3%; S, 9.8%.

Example 6

35 g of L-leucine and 3.5 g each of L-valine and L-isoleucine were dispersed in 300 ml water, and 49.7 g of p-ethylbenzenesulfonic acid (equimolar to leucine) was added thereto, dissolved by heating, and adjusted to pH 1.1. Then, the solution was cooled to precipitate L-leucine p-ethylbenzenesulfonate crystals. The precipitated crystals were recovered by centrifugation, then dissolved in a large amount of hot water, and passed through weakly basic ion exchange resin (OH form) to remove the p-ethylbenzenesulfonic acid. The eluate was crystallized by concentration to give 25 g of free L-leucine crystals. Analysis of the mother liquor indicated that the ratio of precipitation of leucine was 73%, the purity of free L-leucine was 99%, and the content of the other amino acids was 1% or less, and 96% of the impurities before crystallization were removed.

Example 7

35 g of L-leucine and 1.1 g each of L-valine and L-isoleucine were dispersed in 220 ml water, and 49.7 g of p-ethylbenzenesulfonic acid (equimolar to leucine) was added thereto, dissolved by heating, and adjusted to pH 1.1. Then, the solution was cooled to precipitate L-leucine p-ethylbenzenesulfonate crystals. The precipitated crystals were recovered by centrifugation, then dissolved in a large amount of hot water, and passed through weakly basic ion exchange resin (OH form) to remove the p-ethylbenzenesulfonic acid. The eluate was crystallized by Concentration to give 27 g of free L-leucine crystals. Analysis of the mother liquor indicated that the ratio of precipitation of leucine was 80%, the purity of free L-leucine was 99%, and the content of the other amino acids was 1% or less, and 88% of the impurities before crystallization were removed.

Example 8

10 g of D-leucine and 0.3 g each of D-valine and D-isoleucine were added to 65 ml water, and 14.2 g of p-ethylbenzenesulfonic acid (equimolar to leucine) was added thereto, adjusted to pH 1.1 and dissolved by heating. Then, the solution was cooled to precipitate D-leucine p-ethylbenzenesulfonate crystals. The precipitated crystals were recovered by centrifugation, then dissolved in a large amount of hot water, and passed through weakly basic ion exchange resin (OH form) to remove the p-ethylbenzenesulfonic acid. The eluate was crystallized by concentration to give 7.5 g of free D-leucine crystals. Analysis of the mother liquor indicated that the ratio of precipitation of leucine was 80%, the purity of free D-leucine was 99%, and the content of the other amino acids was 1% or less, and 88% of the impurities before crystallization were removed.

Example 9

Figure 4:
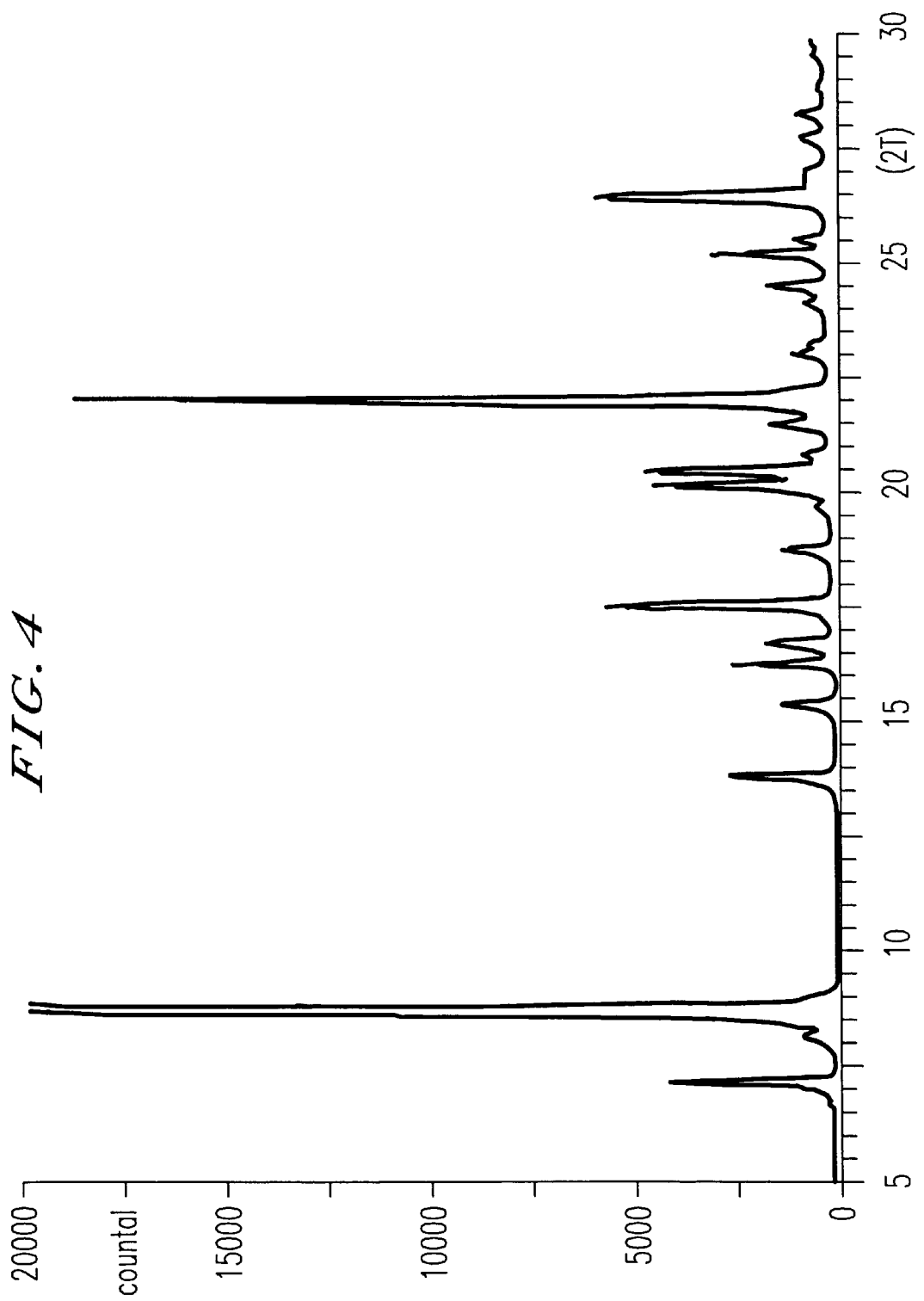
FIG. 4 is an X-ray diffraction pattern of the crystal powder of L-isoleucine p-ethylbenzene sulfonate obtained in Example 9.

400 ml water was added to 100 g of L-isoleucine and 142 g of p-ethylbenzenesulfonic acid, and the temperature of the solution was made 40° C. to dissolve the solid. Then, the solution was cooled at 5° C. to precipitate L-isoleucine p-ethylbenzenesulfonate crystals, and the precipitated crystals were separated by filtration and then dried in vacuo. The resulting L-isoleucine p-ethylbenzenesulfonate was fine white crystal in the monoclinic system with 1.27 g/cm$^3$ of crystal density. An X-ray diffraction pattern of the crystal powder is shown in FIG. 4. The X-ray diffraction was determined using Cu—Kα ray as a radiation source. The result of elemental analysis was C, 53.1%; H, 7.3%; N, 4.3%; S, 9.9%.

Comparative Example 2

400 ml water was added to 100 g of L-isoleucine and 152 g of p-normalpropylbenzene sulfonic acid, and the temperature of the solution was made 40° C. to dissolve the solid. Then, the solution was cooled at 5° C., but no crystal was obtained.

Example 10

35 g of L-isoleucine and 3.5 g each of L-valine and L-leucine were dispersed in 125 ml water, and 49.7 g of p-ethylbenzenesulfonic acid (equimolar to isoleucine) was added thereto, dissolved by heating, and adjusted to pH 1.1. Then, the solution was cooled to precipitate L-isoleucine p-ethylbenzenesulfonate crystals. The precipitated crystals were recovered by centrifugation, then dissolved in a large amount of hot water, and passed through weakly basic ion exchange resin (OH form) to remove the p-ethylbenzenesulfonic acid. The eluate was crystallized by concentration to give 25 g of free L-isoleucine crystals. Analysis of the mother liquor indicated that the ratio of precipitation of isoleucine was 68%, the purity of free L-isoleucine was 96%, and the content of the other amino acids was 4% or less, and 86% of the impurities before crystallization were removed.

Example 11

35 g of L-isoleucine and 1.1 g each of L-valine and L-leucine were dispersed in 100 ml water, and 49.7 g of p-ethylbenzenesulfonic acid (equimolar to isoleucine) was added thereto, dissolved be heating, and adjusted to pH 1.1. Then, the solution was cooled to precipitate L-isoleucine p-ethylbenzenesulfonate crystals. The precipitated crystals were recovered by centrifugation, then dissolved in a large amount of hot water, and passed through weakly basic ion exchange resin (OH form) to remove the p-ethylbenzenesulfonic acid. The eluate was crystallized by concentration to give 28 g of free L-isoleucine crystals. Analysis of the mother liquor indicated that the ratio of precipitation of isoleucine was 85%, the purity of free L-isoleucine was 98%, and the content of the other amino acids was 2% or less, and 75% of the impurities before crystallization were removed.

Example 12

10 g of D-isoleucine and 0.3 g each of D-valine and D-leucine were added to 30 ml water, and 14.2 g of p-ethylbenzenesulfonic acid (equimolar to isoleucine) was added thereto, adjusted to pH 1.1, and dissolved by heating. Then, the solution was cooled to precipitate D-isoleucine p-ethylbenzenesulfonate crystals. The precipitated crystals were recovered by centrifugation, then dissolved in a large amount of hot water, and passed through weakly basic ion exchange resin (OH form) to remove the p-ethylbenzenesulfonic acid. The eluate was crystallized by concentration to give 8 g of free D-isoleucine crystals. Analysis of the mother liquor indicated that the ratio of precipitation of isoleucine was 84%, the purity of free D-isoleucine was 98%, and the content of the other amino acids was 2% or less, and 73% of the impurities before crystallization were removed.

As described above, the amino acid p-ethylbenzenesulfonate crystals obtained by the invention which consists of an amino acid selected from the group consisting of valine, leucine and isoleucine, and of p-ethylbenzenesulfonic acid can introduce said amino acid inexpensively and easily with high purity and thus they are very useful. That is, the operation of producing said amino acid p-ethylbenzenesulfonate crystals and purifying said amino acid can be applied to any amino acid selected from the group consisting of valine, leucine and isoleucine and nevertheless the effect of separating the amino acids from the others is significant due to specificity of said salt. In addition, p-ethylbenzenesulfonic acid can be produced easily in industry by sulfonation of inexpensive ethylbenzene, is easily obtainable, and is further capable of assimilation with microorganisms, so its waste fluid can be treated by active sludge. Hence, the present invention is applicable to industry inexpensively and easily. Further, it is easy to separate and recover said amino acid from said salt and to recover and re-use p-ethylbenzene sulfonic acid from said salt.

The Japanese priority document 9-041980 is incorporated by reference in its entirety.

It will be readily apparent to those skilled in the art that changes and modifications from the preferred embodiments can be made without departing from the spirit and scope of the invention as defined by the following claims.

We claim:

1. A method for purifying valine, leucine and isoleucine, comprising:

in the same purification facility, (1) contacting p-ethylbenzenesulfonic acid or a water-soluble salt thereof with an aqueous solution of valine to precipitate crystals of valine p-ethylbenzenesulfonate, and then separating and decomposing said crystals to obtain valine;

(2) contacting p-ethylbenzenesulfonic acid or a water-soluble salt thereof with an aqueous solution of leucine to precipitate crystals of leucine p-ethylbenzenesulfonate, and then separating and decomposing said crystals to obtain leucine; and (3) contacting p-ethylbenzenesulfonic acid or a water-soluble salt thereof with an aqueous solution of isoleucine to precipitate crystals of isoleucine p-ethylbenzenesulfonate, and then separating and decomposing said crystals to obtain isoleucine.

2. The method of claim 1, wherein the water-soluble salt of p-ethylbenzenesulfonic acid is an alkali metal salt.

3. A method for purifying isoleucine, comprising:

contacting p-ethylbenzene sulfonic acid or a water-soluble salt thereof with an aqueous solution of valine to precipitate crystals of isoleucine p-ethylbenzenesulfonate, and separating and decomposing said crystals to obtain isoleucine.

4. Salt crystals comprising 1 equivalent of isoleucine and 1 equivalent of p-ethylbenzenesulfonic acid.

5. The salt crystals of claim 4, further comprising salt crystals containing 1 equivalent of valine and 1 equivalent of p-ethylbenzenesulfonate.

6. The salt crystals of claim 4, further comprising salt crystals containing 1 equivalent of leucine and 1 equivalent of p-ethylbenzenesulfonate.

* * * * *